United States Patent [19]

Hayakawa et al.

[11] Patent Number: 5,696,132
[45] Date of Patent: Dec. 9, 1997

[54] PYRIDONECARBOXYLIC ACID DERIVATIVES

[75] Inventors: Isao Hayakawa; Youichi Kimura; Hisashi Takahashi, all of Tokyo, Japan

[73] Assignee: Daiichi Pharmaceutical Co., Ltd., Tokyo, Japan

[21] Appl. No.: 142,444

[22] PCT Filed: May 27, 1992

[86] PCT No.: PCT/JP92/00687

§ 371 Date: Jan. 26, 1994

§ 102(e) Date: Jan. 26, 1994

[87] PCT Pub. No.: WO92/21659

PCT Pub. Date: Oct. 12, 1992

[30] Foreign Application Priority Data

May 28, 1991 [JP] Japan ................. 3-225425

[51] Int. Cl.$^6$ ............ A61K 31/47; A61K 31/50; C07D 215/233; C07D 241/04
[52] U.S. Cl. ............ 514/300; 514/312; 546/156; 546/123
[58] Field of Search ............ 546/156, 123; 514/312, 300

[56] References Cited

U.S. PATENT DOCUMENTS

| | | | |
|---|---|---|---|
| 4,920,120 | 4/1990 | Domagala | 514/254 |
| 5,057,520 | 10/1991 | Chu | 514/300 |
| 5,059,597 | 10/1991 | Petersen | 514/224.5 |
| 5,061,712 | 10/1991 | Petersen | 514/300 |
| 5,072,001 | 12/1991 | Hagen | 548/572 |
| 5,137,892 | 8/1992 | Chu | 514/278 |
| 5,140,033 | 8/1992 | Schriewer | 514/312 |
| 5,153,203 | 10/1992 | Yatsunami | 514/312 |
| 5,252,734 | 10/1993 | Schriewer et al. | 544/64 |
| 5,563,138 | 10/1996 | Ueda | 514/254 |
| 5,587,386 | 12/1996 | Hayakawa | 514/312 |

FOREIGN PATENT DOCUMENTS

| | | |
|---|---|---|
| 5231790 | 10/1990 | Australia. |
| 0191185 | 2/1985 | European Pat. Off.. |
| 0341493 | 11/1989 | European Pat. Off.. |
| 3509546 | 9/1986 | Germany. |
| 8700471 | 2/1987 | Netherlands. |
| 2188317 | 9/1987 | United Kingdom. |

OTHER PUBLICATIONS

Remuzon et al, "Fluoronaphthyridines and –Quinolones as Antibacterial Agents. 3. Synthesis and Structure–Activity Relationships of New 1–(1,1–Dimethyl–2–Fluoroethyl), 1–[Methyl–1–(Fluoromethyl)–2–Fluoroethyl], and 1–[1, 1–(Difluoromethyl)–2–Fluororethyl] Substituted Derivatives," *J. Med. Chem.*, 34:29–37 (1991).

Yukimoto et al, "Process for Preparing 8–Chloroquinolone Derivatives", *Chemical Abstracts*, 119(11):117137s (Sep. 13, 1993).

*Primary Examiner*—C. Warren Ivy
*Assistant Examiner*—D. Margaret M. Mach
*Attorney, Agent, or Firm*—Sughrue,Mion,Zinn,Macpeak & Seas, PLLC

[57] ABSTRACT

Quinolone derivatives are known as synthetic antimicrobial agents having a condensed pyridonecarboxylic acid skeleton, and those having substituents on various replaceable positions of said skeleton are known. In particular, if diastereomers exist, there are 4 or more kinds of stereoisomers. A mixture of diastereomers is a mixture of isomers having different physical properties and is difficult to apply as a drug as such. The present invention provides an antimicrobial 1-(1,2-cis-2-fluorocyclopropyl)-substituted quinolone derivative represented by formula I shown below which, although involving diastereomers, consists of a single stereoisomer.

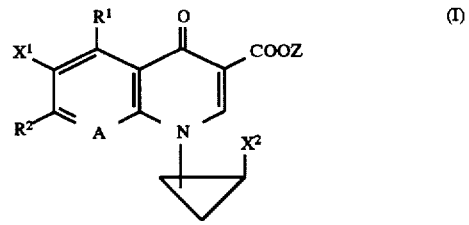

wherein $R^1$ represents a methyl group, a difluoromethyl group, etc.; $R^2$ represents a saturated nitrogen-containing heterocyclic group; A represents C—$X^3$ or a nitrogen atom; $X^1$ and $X^2$ each represents a halogen atom; and $X^3$ and Z represent a hydrogen atom, etc.

11 Claims, No Drawings

PYRIDONECARBOXYLIC ACID DERIVATIVES

This application is a 371 of PCT/JP92/00687, filed May, 27, 1992.

FIELD OF THE INVENTION

This invention relates to an antimicrobial compound useful as human and veterinary drugs, fish drugs, and antimicrobial preservatives, and an antimicrobial agent containing the compound as an active ingredient.

BACKGROUND OF THE INVENTION

Quinolone derivatives are known as synthetic antimicrobial agents having a condensed pyridonecarboxylic acid skeleton. It is known that those having a cyclopropyl group at the 1-position exhibit potent antimicrobial activity. Further, quinolone derivatives having a fluorine atom introduced into the 2-position of the cyclopropyl group in a cis-configuration with respect to the condensed pyridonecarboxylic acid moiety also exhibit potent antimicrobial activity. These quinolone derivatives are considered to have not only potent antimicrobial activity but high safety (see JP-A-62-12760, the term "JP-A" means an "unexamined published Japanese patent application").

Quinolone derivatives having a cis-halogenocyclopropyl group at the 1-position possess excellent properties in terms of antimicrobial activity and safety. These quinolone derivatives embrace a pair of enantiomers attributed to the halogenocyclopropane ring even when the substituent at the other position includes no stereoisomerism, which is ascribed to the stereochemical relationship between the pyridonecarboxylic acid moiety and the halogen atom on the cyclopropane ring. It is possible to apply a racemic compound, a mixture of enantiomers, as a drug as such.

When stereoisomerism exists at a position other than the halogenocyclopropane ring, particularly at the 7-positioned substituent, such quinolone derivatives include diastereomers, that is, at least 4 kinds of stereoisomers. A mixture of diastereomers is a mixture of isomers having different physical properties and is difficult to apply as a drug as such.

The present inventors have conducted extensive investigations for the purpose of obtaining a 1-(1,2-cis-2-fluorocyclopropyl)-substituted quinolone compound which consists of a single isomer even if it may embrace diastereomers.

As a result, the inventors have succeeded in separately obtaining each enantiomer of cis-2-fluorocyclopropylamine as a pure isomer and then separately obtaining each enantiomer of a quinolone derivative attributed only to the stereochemical configuration of the fluorocyclopropane ring thereof by starting with the cis-fluorocyclopropylamine.

Now that the above-mentioned quinolone derivative useful as an intermediate has been obtained, it is possible to synthesize an optically active quinolone derivative consisting solely of a single diastereomer by reacting the quinolone derivative with a saturated nitrogen-containing heterocyclic compound consisting solely of a single isomer at the time of introducing a saturated nitrogen-containing heterocyclic substituent into the 7-position.

And the inventors have ascertained that each of the resulting diastereomers exhibits potent antimicrobial activity and also has high safety with markedly improved selective toxicity and thus completed the present invention.

DISCLOSURE OF THE INVENTION

The present invention relates to a compound represented by formula (I):

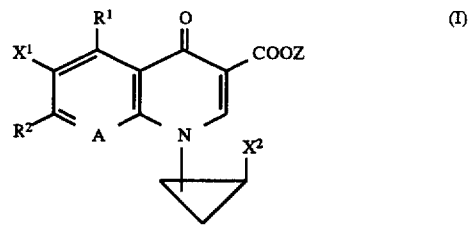

wherein $R^1$ represents a methyl group, an ethyl group, a propyl group, an isopropyl group, a fluoromethyl group or a difluoromethyl group; $R^2$ represents a substituted or unsubstituted saturated nitrogen-containing heterocyclic substituent which may contain an oxygen atom, a sulfur atom or more than one nitrogen atoms as a ring-constituent atom; A represents C—$X^3$ or a nitrogen atom; $X^1$ and $X^2$ each represents a halogen atom; $X^3$ represents a hydrogen atom, a halogen atom, a cyano group, a trifluoromethyl group, an alkyl group having from 1 to 6 carbon atoms or an alkyloxy group having from 1 to 6 carbon atoms; and Z represents a phenylalkyl group composed of an alkylene group having from 1 to 6 carbon atoms and a phenyl group, a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-substituted-2-oxo-1,3-dioxol-4-ylmethyl group, a 3-acetoxy-2-oxobutyl group, an alkyl group having from 1 to 6 carbon atoms or an alkyloxymethyl group having from 2 to 7 carbon atoms, and a salt thereof.

The present invention relates to a compound the formula, wherein $R^2$ is a 4- to 7-membered saturated nitrogen-containing heterocyclic substituent which may be substituted with (1) a hydroxyl group, (2) an alkyl group having from 1 to 6 carbon atoms or (3) amino group which may have a substituent(s), and a salt thereof.

The present invention relates to a compound of the formula, wherein $R^2$ is (1) pyrrolidinyl group which may have a substituent(s), (2) piperidinyl group which may have a substituent(s), (3) piperazinyl group which may have a substituent(s), (4) diazabicycloheptyl group which may have a substituent(s) or (5) diazabicyclooctyl group which may have a substituent(s), and a salt thereof.

The present invention relates to a compound of the formula, wherein $R^2$ is a saturated nitrogen-containing heterocyclic substituent consisting of a single stereoisomer and a salt thereof. In cases where several kinds of stereochemical isomer exist, the terminology "single stereoisomer" as used herein is construed as including not only the case where a compound consists completely solely of a single kind of stereochemical isomer but the case where other stereochemical isomer exist to such an extent that the whole is recognized to be chemically pure. In other words, it is construed as meaning that other stereochemical isomer may exist to some extent as long as the existence gives no substantial influence, for example, on biological activities or physicochemical constants.

The present invention relates to a compound of the formula, wherein the 1,2-cis-halogenocyclopropyl group is a substituent composed of single stereochemical form, and a salt thereof.

The present invention relates to a compound of the formula, wherein the 1,2-cis-halogenocyclopropyl group is a (1R,2S)-2-halogenocyclopropyl group, and a salt thereof.

The present invention relates to a compound of the formula, wherein $R^2$ is a 3-aminopyrrolidinyl group, and a salt thereof.

The present invention relates to a compound of the formula, wherein $R^2$ is a 7-amino-5-azaspiro[2.4]heptan-5-yl group, and a salt thereof.

The present invention relates to a compound of the formula, wherein $X^2$ is a fluorine atom, and a salt thereof.

The present invention relates to a compound selected from the group consisting of 7-[3-amino-1-pyrrolidinyl]-6,8-difluoro-1-(1,2-cis-2-fluorocyclopropyl)-5-methyl-4-oxo-1,4-dihydroquinoline-3-carboxylic acid, 7-[3-amino-1-pyrrolidinyl]-6-fluoro-1-(1,2-cis-2-fluorocyclopropyl)-5-methyl-4-oxo-1,4-dihydroquinoline-3-carboxylic acid, 7-[7-amino-5-azaspiro[2.4]heptan-5-yl]-6,8-difluoro-1-(1,2-cis-2-fluorocyclopropyl)-5-methyl-4-oxo-1,4-dihydroquinoline-3-carboxylic acid, and 7-(7-amino-5-azaspiro[2.4]heptan-5-yl)-6-fluoro-1-(1,2-cis-2-fluorocyclopropyl)-5-methyl-4-oxo-1,4-dihydroquinoline-3-carboxylic acid, and a salt thereof.

The present invention relates to a compound selected from the above-mentioned group which is a compound consisting of a single diastereomer.

The present invention relates to 7-[3-(S)-aminopyrrolidinyl]-6,8-difluoro-1-[(1R,2S)-2-fluorocyclopropyl]-5-methyl-4-oxo-1,4-dihydroquinoline-3-carboxylic acid.

The present invention relates to 7-[3-(S)-aminopyrrolidinyl]-6-fluoro-1-[(1R,2S)-2-fluorocyclopropyl]-5-methyl-4-oxo-1,4-dihydroquinoline-3-carboxylic acid.

The present invention relates to 7-[7-(S)-amino-5-azaspiro[2.4]heptan-5-yl]-6,8-difluoro-1-[(1R,2S)-2-fluorocyclopropyl]-5-methyl-4-oxo-1,4-dihydroquinoline-3-carboxylic acid.

The present invention relates to 7-[7-(S)-amino-5-azaspiro[2.4]heptan-5-yl]-6-fluoro-1-[(1R,2S)-2-fluorocyclopropyl]-5-methyl-4-oxo-1,4-dihydroquinoline-3-carboxylic acid.

The present invention relates to an antimicrobial agent containing the above-mentioned compound as an active ingredient.

The substituents in the compound of the present invention will now be described. Where $X^1$, $X^2$ and $X^3$ each represent a halogen atom, it is preferable that $X^1$ and $X^3$ represent a fluorine atom or a chlorine atom, and it is particularly preferable that $X^2$ represents a fluorine atom.

$R^1$ is suitably an alkyl group or a halogenoalkyl group, preferably a methyl group, an ethyl group, an n-propyl group, an isopropyl group, a fluoromethyl group or a difluoromethyl group, and more preferably a methyl group.

It is the characteristic feature of the compounds of the present invention that a substituent is present at the 5-position thereof and show potent antibacterial activity. Especially, even when the saturated nitrogen-containing substituent (a detailed discussion about this is given later) at 7 is piperazine, the compounds of the present invention have revealed to have more potent antibacterial activity than the previously known quinolones of a substituent.

$R^2$ represents a saturated nitrogen-containing heterocyclic substituent. A saturated nitrogen-containing heterocyclic group is a substituent derived from a saturated nitrogen-containing heterocyclic compound, i.e., a substituent derived from an alicyclic compound with its carbon atom constituting the cyclic structure being replaced with a nitrogen atom. A preferred ring size is from a 4-membered ring to a 7-membered ring, with a 5- or 6-membered ring being particularly preferred. The ring may contain an oxygen atom, a sulfur atom or a plurality of nitrogen atoms as a ring-constituent atom as in oxazolidine, morpholine, thiazolidine, thiomorpholine, imidazolidine, pyrazolidine and piperazine rings. Of the saturated nitrogen-containing heterocyclic groups, preferred are a pyrrolidinyl group and a piperazinyl group, which may further have a substituent(s).

While the nitrogen-containing heterocyclic substituent is preferably saturated as previously stated, it may contain an unsaturated bond. Examples of such a nitrogen-containing heterocyclic substituent include a 3-pyrrolin-3-yl group, a 3-pyrrolin-2-yl group, a 1,2,5,6-tetrahydropyridin-4-yl group, a 1,2,5,6-tetrahydropyridin-3-yl group, a 1,2,5,6-tetrahydropyridin-2-yl group, a 1,2,5,6-tetrahydropyridin-5-yl group, and a 1,2,5,6-tetrahydropyridin-6-yl group.

The saturated nitrogen-containing heterocyclic substituent may have a substituent(s). The substituents include polar groups, such as (1) amino group which may have a substituent(s), (2) aminoalkyl group which may have a substituent(s), (3) a 5-substituted-2-oxo-1,3-dioxol-4-ylmethyl group, and (4) a hydroxyl group; and (5) a straight chain, branched or cyclic alkyl group having from 1 to 6 carbon atoms. The polar substituent may be bonded to the saturated nitrogen-containing heterocyclic substituent via an alkylene group having from 1 to 6 carbon atoms. The example of the substituent on the amino group includes an alkyl group, an acyl group, and an acyloxycarbonyl group.

The above-mentioned polar group preferably includes an unsubstituted amino group, an aminomethyl group, a 1-aminoethyl group, and a hydroxyl group.

The alkyl group on the saturated nitrogen-containing heterocyclic substituent preferably includes a methyl group, an ethyl group, a propyl group, an isopropyl group, gem-dimethyl groups, gem-diethyl groups, and further, these gem-alkyl groups forms a cyclopropane ring or a cyclobutane ring to provide a spiro cyclic ring system are also preferred. The 4- to 7-membered saturated nitrogen-containing heterocyclic substituent may be crosslinked to form a bicyclic saturated nitrogen-containing heterocyclic group.

Among these saturated nitrogen-containing heterocyclic substituents, examples of those which are substituted with an amino group or those having a second nitrogen atom are shown below.

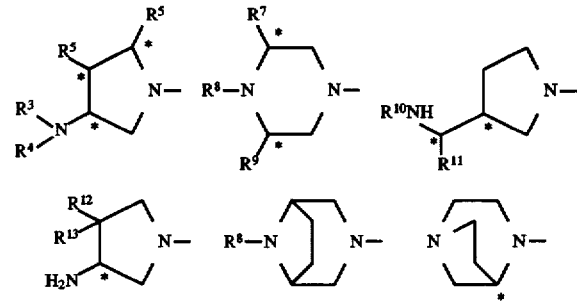

wherein $R^3$, $R^4$, $R^5$, $R^6$, $R^7$, $R^8$, $R^9$, $R^{10}$, $R^{11}$, $R^{12}$ and $R^{13}$ each represents a hydrogen atom or an alkyl group having from 1 to 6 carbon atoms; and $R^{12}$ and $R^{13}$ may be taken together to form a polymethylene chain to provide a 3- to 6-membered ring.

Specific examples of these substituents are a 3-aminopyrrolidinyl group, a 3-methylaminopyrrolidinyl group, a 3-dimethylaminopyrrolidinyl group, a 3-ethylaminopyrrolidinyl group, a 3-propylaminopyrrolidinyl group, a 3-isopropylaminopyrrolidinyl group, a 3-amino-4-methylpyrrolidinyl group, a 4-amino-2-methylpyrrolidinyl group, a 4-amino-2,3-dimethylpyrrolidinyl group, a 3-methylamino-4-methylpyrrolidinyl group, a 4-methylamino-2-methylpyrrolidinyl group, a 4-methylamino-2,3-dimethylpyrrolidinyl group, a 3-dimethylamino-4-methylpyrrolidinyl group, a 4-dimethylamino-2-methylpyrrolidinyl group, a 4-dimethylamino- 2,3-dimethylpyrrrolidinyl group, a 3-methylpiperazinyl group, a 4-methylpiperazinyl group, a 3,4-dimethylpiperazinyl group, a 3,5-dimethylpiperazinyl group, a 3,4,5-trimethylpiperazinyl group, a 4-ethyl-3,5-dimethylpiperazinyl group, a 4-isopropyl-3,5-dimethylpiperazinyl group, a 3-aminomethylpyrrolidinyl group, a 3-methylaminomethylpyrrolidinyl group, a 3-(1-amino)ethylpyrrolidinyl group, a 3-(1-methylamino)ethylpyrrolidinyl group, a 3-(1-ethylamino)ethylpyrrolidinyl group, a 3-(1-amino)propylpyrrolidinyl group, a 3-(1-methylamino)propylpyrrolidinyl group, a 3-aminopyrrolidinyl group, a 4-amino-3,3-dimethylpyrrolidinyl group, a 7-amino-5-azaspiro[2.4]heptan-5-yl group, a 8-amino-6-azaspiro[3.4]octan-6-yl group, a 1,4-diazabicyclo[3.2.1]octan-4-yl group, a 3,8-diazabicyclo[3.2.1]octan-3-yl group, a 8-methyl-3,8-diazabicyclo[3.2.1]octan-3-yl group, and a 8-ethyl-3,8-diazabicyclo[3.2.1]octan-3-yl group.

The structure of the saturated nitrogen-containing heterocyclic substituent at the 7-position influences antimicrobial activity, toxicity, oral absorbability or physicochemical properties such as and water-solubility of the quinolone derivatives.

For example, the inventors found that introduction of a 3-aminopyrrolidinyl group as a substituent furnishes a quinolone compound having strong antimicrobial activity against a broad range of bacteria from Gram-negative to positive. However, some of quinolone compounds having a 3-aminopyrrolidinyl group are observed to be easily metabolised or to have inferior physicochemical properties.

Quinolone compounds with an aminopyrrolidinyl group having a spiro ring in which a spiro ring is construed on the carbon atom adjacent to the amino-substituted carbon atom exhibit improved absorbability and improved to in vivo metabolic stability as well as potent antimicrobial activity. The inventors have also found this substituent excellent to have an effect of less convulsion-inducing action, which is known as a side effect of quinolone compounds is diminished.

Further, quinolone compounds having an aminomethylpyrrolidine group in which an amino group is bonded to the pyrrolidine ring via a carbon atom exhibit excellent effects such as enhanced antimicrobial activity on Gram-positive bacteria. Besides, those in which the carbon atom is substituted with one or two alkyl groups show improved oral absorbability, safety, water-solubility, and so on, compared those in which the carbon atoms is unsubstituted.

In addition to the above-described pyrrolidine groups, piperazine groups are also excellent substituents, and alkylpiperazine groups and spiro-ring-containing piperazine groups are also substituents providing excellent quinolone compounds.

Examples of saturated nitrogen-containing heterocyclic groups having a substituent(s) other than an amino substituent include a 3-hydroxypyrrolidinyl group, a 3-mercaptopyrrolidinyl group, a 3-hydroxy-4-methylpyrrolidinyl group, a 3-mercapto-4-methylpyrrolidinyl group, a morpholino group, a thiomopholino group, a 2-methylmorpholino group, a 2-methylthiomorpholino group, a 2,6-dimethylmorpholino group, a 2,6-dimethylthiomorpholino group, a 2,2-dimethylmorpholino group, and a 2,2-dimethylthiomorpholino group.

In the saturated nitrogen-containing heterocyclic substituents previously illustrated as an amino-substituted saturated nitrogen-containing heterocyclic substituent, where the substituents from $R^1$ to $R^{13}$ each represent a hydrogen atom or an alkyl group having from 1 to 6 carbon atoms, and $R^{12}$ and $R^{13}$ may be taken together to form a polymethylene chain to give a 3- to 6-membered ring, one or more of $R^3$ or $R^4$, $R^5$, $R^6$, $R^7$, $R^8$, $R^9$, $R^{10}$, and $R^{12}$ or $R^{13}$ may be a hydroxyl group, or one or more of $R^3$ or $R^4$, $R^5$, $R^6$, $R^7$, $R^8$, $R^9$, $R^{10}$, and $R^{12}$ or $R^{13}$ may be an alkyloxy group having from 1 to 6 carbon atoms.

$R^2$ may be an aminocycloalkenyl group whose structure is similar to the saturated nitrogen-containing heterocyclic substituent, e.g., a 3-aminocyclopenten-1-yl group, a 3-aminocyclopenten-2-yl group, a 3-aminocyclopenten-3-yl group, a 3-aminocyclopenten-4-yl group, a 3-aminocyclopenten-5-yl group, a 3-aminocyclohexen-1-yl group, a 3-aminocyclohexen-2-yl group, a 3-aminocyclohexen-3-yl group, a 3-aminocyclohexen-4-yl group, a 3-aminocyclohexen-5-yl group or a 3-aminocyclohexen-6-yl group.

It is particularly preferable that the saturated nitrogen-containing heterocyclic substituent is bonded to the 7-position of the quinolone nucleus at the nitrogen atom thereof. Those compound with its saturated nitrogen-containing heterocyclic substituent being bonded at the carbon atom thereof are also included under the scope of the present invention.

The stereoisomerism of the saturated nitrogen-containing heterocyclic substituent at the 7-position will be explained. Where stereoisomerism exists in a saturated nitrogen-containing heterocyclic compound necessary for introducing a saturated nitrogen-containing heterocyclic substituent, if a saturated nitrogen-containing heterocyclic compound in the form of a mixture of optical isomers is used as a starting material to be reacted with a quinolone nuclear compound, the resulting quinolone derivative is a mixture of diastereomers because of the stereoisomerical relationship of the 1,2-cis-2-halogenocyclopropyl group at the 1-position. Therefore, where stereoisomerism exists in a saturated nitrogen-containing heterocyclic compound, it is preferable to use one of the isomers alone as a starting material to be reacted with a quinolone compound.

At introduction of a saturated nitrogen-containing heterocyclic substituent to the 7-position of quinolone, a functional group on the amine ring, e.g., an amino group, a hydroxyl group or a mercapto group, may be protected with a commonly employed protective group. Specific examples of the protective group are alkyloxycarbonyl groups, e.g., a t-butoxycarbonyl group and a 2,2,2-trichloroethoxycarbonyl group; aralkyloxycarbonyl groups, e.g., a benzyloxycarbonyl group, a p-methoxybenzyloxycarbonyl group and a p-nitrobenzyloxycarbonyl group; acyl groups, e.g., an acetyl group, a methoxyacetyl group, a trifluoroacetyl group, a chloroacetyl group, a pivaloyl group, a formyl group, and a benzoyl group; alkyl groups or aralkyl groups, e.g., a t-butyl group, a benzyl group, a p-nitrobenzyl group, a para-methoxybenzyl group and a triphenylmethyl group; ether groups, e.g., a methoxymethyl group, a t-butoxymethyl group, a tetrahydropyranyl group, and a 2,2,2-trichloroethoxymethyl group; and silyl groups, e.g., a trimethylsilyl group, an isopropyldimethylsilyl group, a t-butyldimethylsilyl group, a tribenzylsilyl group, and a t-butyldiphenylsilyl group.

The 1,2-cis-halogenocyclopropyl group at the $N_1$-position will be described below.

In the compounds of the present invention, the cyclopropyl group is substituted with a halogen atom, particularly a fluorine atom, which brings about reduction in lipophilicity of the whole molecule. The present inventors considered that a drug is distributed to the central nervous system more easily with the increase in lipophilicity so that the $N_1$-(1,2-cis-2-halogenocyclopropyl)-substituted pyridonecarboxylic acid derivative of the present invention would be a less toxic quinolone derivative. The halogen atom as a substituent includes a fluorine atom and a chlorine atom and is preferably a fluorine atom.

A particularly preferred stereochemical circumstance in this moiety is that the halogen atom and the pyridonecarboxylic acid moiety are in a cis-configuration with respect to the cyclopropane ring. Enantiomers exist depending on only the cis-2-halogenocyclopropyl moiety at the 1-position irrespective of the stereoisomerism of the 7-positioned saturated nitrogen-containing heterocyclic substituent. Either of the enantiomers was observed to have potent antimicrobial activity and high safety.

The pyridonecarboxylic acid derivative of the present invention may be either a free form or a form of an acid addition salt or a salt at the carboxyl group. Acid addition salts include inorganic acid salts, such as hydrochlorides, sulfates, nitrates, hydrobromides, hydroiodides, and phosphates; and organic acid salts, such as acetates, metanesulfonates, benzenesulfonates, toluenesulfonates, citrates, maleates, fumarates, and lactates.

Salts at the carboxyl group include both inorganic salts and organic salts, such as alkali metal salts, e.g., lithium salts, sodium salts, and potassium salts; alkaline earth metal salts, e.g., magnesium salts and calcium salts; ammonium salts; triethylamine salts, N-methylglucamine salts, and tris-(hydroxymethyl)aminomethane salts.

The free pyridonecarboxylic acid derivatives, acid addition salts thereof, and salts thereof at the carboxyl group may be present as a hydrate.

On the other hand, quinolone derivatives with the carboxylic acid moiety thereof having an ester form are useful as a synthetic intermediate or a pro-drug (a drug precursor). For example, alkyl esters, benzyl esters, alkyloxyalkyl esters, phenylalkyl esters, and phenyl esters are useful as synthetic intermediates.

Esters which can be used as pro-drugs are esters which are easily severed in vivo to produce a free carboxylic acid, including acetoxymethyl esters, pivaloyloxymethyl esters, ethoxycarbonyl esters, choline esters, dimethylaminoethyl esters, 5-indanyl esters, phthalidinyl esters, 5-substituted-2-oxo-1,3-dioxol-4-ylmethyl esters, and oxoalkyl esters, such as 3-acetoxy-2-oxobutyl esters.

A process for preparing the compounds according to the present invention is explained below by way of an illustrative example.

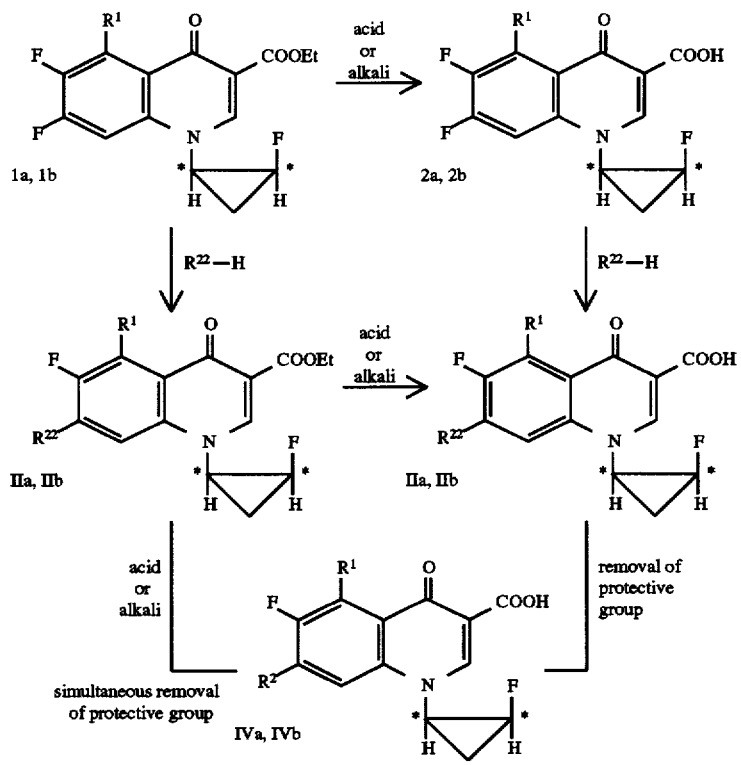

wherein $R^{22}$ represents a protected $R^2$ substituent or the same saturated nitrogen-containing heterocyclic substituent as $R^2$.

An optically active 1-(1,2-cis-2-fluorocyclopropyl)-6,7-difluoro-4-oxo-1,4-dihydroquinoline-3-carboxylic acid ester 1a or 1b is hydrolyzed under an acidic or alkaline condition to give a free carboxylic acid derivative 2a or 2b. Compound 2a or 2b is then reacted with a saturated nitrogen-containing heterocyclic compound $R^{22}$—H to give a desired compound IIIa or IIIb. If necessary, a protective group is removed under conditions selected suitable for the protective group to give a desired compound IVa or IVb. The substitution reaction with the saturated nitrogen-containing heterocyclic compound is carried out in a solvent, such as dimethyl sulfoxide, pyridine, acetonitrile or 3-methoxybutanol, at a temperature of from room temperature to 150° C., and preferably from 40° to 120° C. The reaction time ranges from 30 minutes to 5 hours and usually from 30 minutes to 2 hours.

Alternatively, compound 1a or 1b is reacted with a saturated nitrogen-containing heterocyclic compound under conditions similar to those described above, and the resulting compound IIa or IIb is hydrolyzed under an acidic or alkaline condition without being isolated and purified and, if necessary, treated to remove a protective group to yield a desired compound IIIa or IIIb or IVa or IVb.

The intermediate, an optically active saturated nitrogen-containing heterocyclic compound, e.g., cis-2-fluorocyclopropylamine, can be synthesized as follows.

2-Fluorocyclopropanecarboxylic acid is reacted with (R)-(+)-α-methylbenzylamine to yield N-[1-(R)-phenylethyl]-1,2-cis-2-fluorocyclopropanecarboxamide. This reaction can be carried out in tetrahydrofuran in the presence of N,N'-carbonyldiimidazole or in accordance with a mixed acid anhydride method. In the mixed acid anhydride method, the carboxylic acid is dissolved in an aprotic solvent and reacted with a halogenoformic ester in the presence of a base in a low temperature. The reaction product is then reacted with the above-mentioned benzylamine, and the reaction mixture is worked up in a known manner to yield a carboxamide. The resulting carboxamide is chromatographically separated into each enantiomer of N-[1-(R)-phenylethyl]-1,2-cis-2-fluorocyclopropanecarboxamide.

The solvent used in the mixed acid anhydride method preferably includes aprotic solvents, such as ethers, e.g., diethyl ether, diisopropyl ether, tetrahydrofuran, 1,4-dioxane, and 1,2-dimethoxyethane; halogenated hydrocarbons, e.g., dichloromethane, chloroform, 1,2-dichloroethane, and 1,1,2,2-tetrachloroethane; aromatic hydrocarbons, e.g., benzene, toluene, and xylene; and aliphatic hydrocarbons, e.g., pentane, hexane, heptane, and cyclohexane. Of these solvents, generally employed are tetrahydrofuran, chloroform, etc. In carrying out the reaction, the water content of the solvent is generally removed beforehand.

The halogen atom in the halogenoformic ester is usually a chlorine atom. The esters include those of methyl, ethyl, 2,2,2-trichloroethyl, phenyl, p-nitrophenyl, benzyl, etc.

The bases to be used may be either inorganic or organic. Examples of inorganic bases include hydroxides, carbonates, or hydrogencarbonates of alkali metals, such as lithium hydroxide, sodium hydroxide, potassium hydroxide, lithium carbonate, sodium carbonate, potassium carbonate, sodium hydrogencarbonate, and potassium hydrogencarbonate.

Examples of organic bases include trialkylamines, e.g., triethylamine, tripropylamine, tributylamine, and N,N-diisopropylethylamine; dialkylanilines, e.g., diethylaniline and dimethylaniline; and saturated or aromatic heterocyclic compounds, e.g., N-methylmorpholine, pyridine, and N,N-dimethylaminopyridine.

Separation of the produced carboxamide into optical isomers can be performed in a usual manner by silica gel column chromatography, silica gel column chromatography under pressure, preparative TLC, high performance liquid chromatography, and so forth. It is also possible to separate into optical isomers through generally employed separation techniques other than chromatography, such as recrystallization, reprecipitation, and the like.

The thus separated optically active carboxamide compound is led to an optically active cis-2-fluorocyclopropanecarboxylic acid by heating in an acidic condition. The heating is effected by, for example, dissolving the carboxamide in concentrated hydrochloric acid followed by heating. Sulfuric acid, nitric acid, etc. may also be used as the acid. The reaction may also be carried out in the presence of a solvent, such as acetic acid, a lower alcohol, etc.

The carboxylic acid is subjected to Curtius reaction in the presence of t-butanol to be converted directly to protected cis-1-(t-butoxycarbonylamino)-2-fluorocyclopropane. While this reaction can be carried out conveniently by using diphenylphosphoryl azide, synthesis of the intermediate azide compound is not limited thereto, and usual synthetic processes may be applied.

Starting with the thus obtained optically active cis-2-fluorocyclopropylamine derivative, a quinolone derivative having a cis-fluorocyclopropyl group at the 1-position can be obtained as a single isomer, which is then reacted with a saturated nitrogen-containing heterocyclic compound as described above to obtain a quinolone derivative of the present invention.

The compounds of the present invention have potent antimicrobial activity and are therefore useful as drugs for humans, animals, and fishes, agricultural chemicals, or food preservatives.

For use as drugs for humans, the dose of the compound of the present invention is in the range of from 50 mg to 1 g, and preferably from 100 mg to 300 mg, per day for adults.

For veterinary use, the dose is generally in the range of from 1 to 200 mg, and preferably from 5 to 100 mg, per kg of body weight per day while varying depending on the purpose of administration (for therapy or for prevention), the kind and the size of the animal, the kind of the pathogenic organisms, and the symptom.

The above-mentioned daily dose is given once a day or in 2 to 4 divided doses. If necessary, a daily dose may exceed the above-specified range.

The compounds according to the present invention are active on a very broad range of microorganisms causing various infectious diseases and effective to prevent, alleviate or cure diseases caused by these pathogenes. Examples of bacteria or bacterium-like microorganisms on which the compounds of the present invention are effective include staphylococci, *Streptococcus pyogenes, Streptococcus haemolyticus, Streptococcus fecalis, Streptococcus pneumoniae,* peptostreptococci, *Neisseria gonorrhoeae, Escherichia coli,* Citrobacter sp., Shigella sp., *Klebsiella pneumoniae,* Enterobacter sp., Serratia sp., Proteus sp., *Pseudomonas aeruginosa, Haemophilus influenzae,* Acinetobacter sp., Camplobacter sp., and *Chlamydozoon trachomatis.*

Diseases which are caused by these pathogenes include folliculitis, furuncle, carbuncle, erysipelas, phlegmon, lymphangitis/lymphadenitis, felon, subcutaneous abscess, spiradenitis, acne conglobata, infectious atheroma, perianal abscess, mastadenitis, superficial secondary infections after trauma, burn or surgery trauma, pharyngolaryngitis, acute bronchitis, tonsillitis, chronic bronchitis, bronchiectasis, diffuse panbronchiolitis, secondary infections of chronic respiratory diseases, pneumonia, pyelonephritis, cystiris, prostatitis, epididymitis, gonococcal urethritis, non-gonococcal urethritis, cholecystitis, cholangitis, bacillary dysentery, enteriris, adnexitis, intrauterine infections, bartholinitis, blepharitis, hordeolum, dacryocystitis, tarsadenitis, keratohelcosis, otitis media, sinusitis, paradentosis, pericoronitis, gnathitis, peritonitis, endocarditis, septicemia, meningitis, and skin infections.

The compounds of the present invention are also effective on various microorganisms causing veterinary diseases, such as those belonging to the genera Escherichia, Salmonella, Pasteurella, Haemophilus, Bordetella, Staphylococcus, and Mycoplasma. Illustrative examples of the veterinary diseases include those of fowl, such as colibacillosis, pullorum disease, avian paratyphosis, fowl cholera, infectious coryza, staphylomycosis, and mycoplasmosis; those of pigs, such as colibacillosis, salmonellosis, pasteurellosis, hemophilus infections, atrophic rhinitis, exudative epidermitis, and mycoplasmosis; those of cattle, such as colibacillosis, salmonellosis, hemorrhagic septicemia, mycoplasmosis, bovine contagious pleuropneumonia, and bovine mastitis; those of dogs, such as colisepsis, salmonellosis, hemorrhagic septicemia, pyometra, and cystitis; those of cats, such as exudative pleurisy, cystitis, chronic rhinitis, and hemophilus infections; and those of kittens, such as bacterial diarrhea and mycoplasmosis.

Dosage forms of the pharmaceutical preparations containing the compound of the present invention are appropriately selected according to the administration route and can be prepared by conventional preparation methods. Examples of dosage forms for oral administration include tablets, powders, granules, capsules, solutions, syrups, elixirs, and oily or aqueous suspensions.

Injectable preparations may contain adjuvants, such as stabilizers, antiseptics, and solubilizers. The injectable solution which may contain these adjuvants may be put into a container and solidified by, for example, lyophilization to prepare a solid preparation which is dissolved on use. The container may contain either a single dose or multiple doses.

Preparations for external application include solutions, suspensions, emulsions, ointments, gels, creams, lotions, and sprays.

Solid preparations may contain, in addition to the active compound, pharmaceutically acceptable additives. For example, the active compound is mixed with additives selected according to necessity from among fillers, extenders, binders, disintegrators, absorption accelerators, wetting agents, and lubricants and formulated into solid preparations.

Liquid preparations include solutions, suspensions, and emulsions. They may contain adjuvants, such as suspending agents, emulsifiers, and so forth.

The compound can be administered to animals orally either directly or by mixing with feedstuff, or in a dissolved form directly given to animals or by mixing with water or feedstuff or non-orally by injection.

For veterinary use, the compound can be formulated into powders, fine granules, soluble powders, syrups, solutions, and injections according to the customary methods in the art.

Formulation Examples of the present invention are illustrated below.

FORMULATION EXAMPLE 1

| Capsules | |
|---|---|
| Compound of Example 9 | 100.0 mg |
| Corn starch | 23.0 mg |
| CMC · Ca | 22.5 mg |
| Hydroxymethyl cellulose | 3.0 mg |
| Magnesium stearate | 1.5 mg |
| Total: | 150.0 mg |

FORMULATION EXAMPLE 2

| Solution | |
|---|---|
| Compound of Example 7 | 1–10 g |
| Acetic acid or sodium hydroxide | 0.5–2 g |
| Ethyl p-hydroxybenzoate | 0.1 g |
| Purified water | 88.9–98.4 g |
| Total: | 100 g |

FORMULATION EXAMPLE 3

| Powder for Mixing with Feed | |
|---|---|
| Compound of Example 10 | 1–10 g |
| Corn starch | 98.5–89.5 g |
| Light anhydous silicic acid | 0.5 g |
| Total: | 100 g |

MOST PREFERRED EMBODIMENT FOR CARRYING OUT THE INVENTION

The present invention will now be illustrated by way of Examples and Reference Examples, but the present invention should not be construed as being limited thereto. Antimicrobial activity of the optically active compounds obtained was determined in accordance with the standard method specified by Japan Chemotherapy Institute, and the results obtained are shown in Table 1 below in terms of MIC (μg/ml).

REFERENCE EXAMPLE 1

N-[1-(R)-Phenylethyl]-1,2-cis-2-fluorocyclopropanecarboxamide 4a, 4b 1-1. Carbonyldiimidazole Method:

In 30 ml of tetrahydrofuran (hereinafter abbreviated as THF) was dissolved 1.0 g of cis-2-fluorocyclopropanecarboxylic acid, and 1.78 g of N,N'-carbonyldiimidazole was added thereto, followed by stirring at room temperature for 1 hour. To the mixture was added 1.45 g of (R)-(+)-α-methylbenzylamine, and the stirring was continued for further 2 hours. The solvent was removed under reduced pressure, and the residue was extracted with chloroform. The extract was washed successively with a 10% citric acid aqueous solution and water and dried, and the solvent was removed under reduced pressure. The residual viscous oily substance was subjected to high performance liquid chromatography for separation into each stereoisomer. Each stereoisomer was recrystallized from diisopropyl ether to yield compounds 4a and 4b.

Conditions for Separation:

Column: Nuceosil 50-5 (20 mm (ID)×250 mm (L)), produced by Senshu Kagaku; Senshu Pack SSC silica, 782-IN) Solvent: Ethyl acetate/THF (9:1) Flow rate: 9.0 ml/min Retention time: 11 min for compound 4a 13 min for compound 4b Compound 4a:

Melting point: 108° C. Elementary analysis for $C_{12}H_{14}FNO$: Calcd.: C 69.55; H 6.81; N 6.76 Found: C 69.31; H 7.01; N 6.65 $[\alpha]_D$: +61.96° (c=0.965; chloroform) $^1$H-NMR (CDCl$_3$) δ ppm: 0.92–1.34 (2H, m), 1.50 (3H, d, J=7 Hz), 1.50–1.96 (1H, m), 4.68 (1H, dm, J=64 Hz), 5.14 (1H, m), 7.4 (5H, s)

Compound 4b:

Melting point: 102° C. Elementary analysis for $C_{12}H_{14}FNO$: Calcd.: C 69.55; H 6.81; N 6.76 Found: C 69.45; H 6.87; N 6.70 $[\alpha]_D$: +143.61° (c=0.830; chloroform) $^1$H-NMR (CDCl$_3$) δ ppm: 0.98–1.34 (2H, m), 1.52 (3H, d, J=7 Hz), 1.64–1.96 (1H, m), 4.58 (1H, dm, J=66 Hz), 5.24 (1H, m), 7.40 (5H, m)

1-2. Mixed Acid Anhydride Method:

In 50 ml of THF were dissolved 4.19 g of 2-fluorocyclopropanecarboxylic acid (a cis-trans mixture) and 4.07 g of triethylamine, and the solution was cooled to −10° C. To the solution was added dropwise a solution of 4.73 g of ethyl chloroformate in 20 ml of THF and, after stirring for 10 minutes, a solution of 4.88 g of (R)-(+)-α-methylbenzylamine in 30 ml of THF was further added thereto dropwise at that temperature, followed by stirring at room temperature for 15 hours. The solvent was removed under reduced pressure, and the residue was extracted with benzene. The extract was washed successively with a 10% citric acid aqueous solution, a 1N sodium hydroxide aqueous solution, and water and dried over anhydrous sodium sulfate. The solvent was removed under reduced pressure, and the residual pale yellow oily substance was purified by silica gel column chromatography using a mixed solvent of benzene and ethyl acetate as an eluent to yield compounds 4a and 4b.

REFERENCE EXAMPLE 2

(−)-Cis-2-Fluorocyclopropanecarboxylic Acid 5a

In 15 ml of concentrated hydrochloric acid was dissolved 530 mg of amide compound 4a, and the solution was heated at 100° to 110° C. for 5 hours with stirring. To the reaction mixture was added 20 ml of water, and the mixture was extracted with ethyl acetate. The extract was extracted with a sodium hydrogencarbonate aqueous solution and washed with ethyl acetate. The aqueous layer was adjusted to pH 5 with concentrated hydrochloric acid and extracted with ethyl acetate. The extract was dried over anhydrous sodium sulfate, and the solvent was removed under reduced pressure to yield the titled compound as a pale yellow oily substance.

$[\alpha]_D$: −23.13° (c=1.020, chloroform) $^1$H-NMR (CDCl$_3$) δ ppm: 1.0–1.42 (1H, m), 1.60–2.10 (2H, m), 4.82 (1H, dm, J=65 Hz), 12.0 (1H, s)

REFERENCE EXAMPLE 3

(+)-Cis-2-Fluorocyclopropanecarboxylic Acid 5b

In 30 ml of concentrated hydrochloric acid was dissolved 1.65 g of amide compound 4b, and the solution was heated at 100° to 110° C. for 5 hours while stirring. The reaction mixture was adjusted to pH 8–9 with sodium hydrogencarbonate and washed with chloroform. The aqueous layer was adjusted to pH 4 with concentrated hydrochloric acid and extracted with ethyl acetate. The extract was dried over anhydrous sodium sulfate, and the solvent was removed under reduced pressure to yield the titled compound as a pale yellow oily substance.

$[\alpha]_D$: +21.56° (c=1.113, chloroform) $^1$H-NMR (CDCl$_3$) δ ppm: 1.0–1.42 (1H, m), 1.56–1.98 (2H, m), 4.76 (1H, dm, J=66 Hz), 11.32 (1H, s)

REFERENCE EXAMPLE 4

(+)-Cis-1-(t-butoxycarbonylamino)-2-fluorocyclopropane 6a

In 5 ml of t-butanol were dissolved 200 mg of carboxylic acid 5a obtained in Reference Example 2, 603 mg of diphenylphosphoryl azide, and 203 mg of triethylamine, and the solution was heated under reflux for 4.5 hours. The solvent was removed under reduced pressur, and the residue was extracted with chloroform. The extract was washed with a 10% citric acid aqueous solution, a 2% sodium hydroxide aqueous solution, and water, and dried over anhydrous sodium sulfate. The solvent was removed under reduced pressure, and the residue was subjected to silica gel column chromatography using chloroform as an eluent to obtain the titled compound as a colorless crystal.

Melting point: 73° C. $[\alpha]_D$: +65.57° (c=0.610, chloroform) $^1$H-NMR (CDCl$_3$) δ ppm: 0.6–1.3 (2H, m), 1.46 (9H, s), 2.50–2.76 (1H, m), 4.62 (1H, dm, J=65 Hz), 4.5–5.0 (1H, broad)

REFERENCE EXAMPLE 5

(−)-Cis-1-(t-butoxycarbonylamino)-2-fluorocyclopropane 6b

In 6 ml of t-butanol were dissolved 265 mg of carboxylic acid 5b obtained in Reference Example 3, 800 mg of diphenylphosphoryl azide, and 270 mg of triethylamine. The solution was worked up in the same manner as in Reference Example 4 to yield the titled compound as a colorless crystal.

Melting point: 63° C. $[\alpha]_D$: −60.27° (c=0.740, chloroform) $^1$H-NMR (CDCl$_3$) δ ppm: 0.66–1.3 (2H, m), 1.46 (9H, s), 2.48–2.74 (1H, m), 4.58 (1H, dm, J=65 Hz), 4.6–5.1 (1H, broad)

The product was identified to be (1R,2S)-1-(t-butoxycarbonylamino)-2-fluorocyclopropane from X-ray analysis of the quinolone derivative derived therefrom.

REFERENCE EXAMPLE 6

Synthesis of Optically Active 7-Amino-5-azaspiro [2.4]heptane 1) 5-[(1R)-Phenylethyl]-4,7-dioxo-5-azaspiro[2.4] heptane 10:

A mixture of 10.4 g of ethyl acetoacetate, 15 g of 1,2-dibromoethane, 23 g of potassium carbonate, and 150 ml of N,N-dimethylformamide (DMF) was stirred at room temperature for 2 days. An insoluble material was removed by filtration, and the filtrate was concentrated to dryness under reduced pressure. Water was added to the residue, and the mixture was extracted with chloroform. The extract was dried over anhydrous sodium sulfate, and the solvent was removed under reduced pressure. The resulting pale yellow oily substance was distilled under reduced pressure to give 7.5 g of ethyl 1-acetyl-1-cyclopropanecarboxylate as a fraction having a boiling point of 70° to 71° C./2–3 mmHg.

$^1$H-NMR (CDCl$_3$) δ ppm: 1.30 (3H, t, J=7 Hz), 1.48 (4H, s), 2.49 (3H, s), 4.24 (2H, q, J=7 Hz)

In 200 ml of ethanol was dissolved 35.7 g of the resulting compound, and 40 g of bromine was added thereto dropwise at room temperature while stirring. After stirring at room temperature for 2 hours, excess of bromine and the solvent were removed under reduced pressure to yield ethyl 1-bromoacetyl-1-cyclopropanecarboxylate. The product as obtained was dissolved in 200 ml of ethanol, and 33 g of R-(+)-1-phenylethylamine and 27 g of triethylamine were simultaneously added dropwise to the solution over 1 hour under ice-cooling and stirring. The temperature was elevated to room temperature, and the stirring was continued for 2 days. An insoluble material was removed by filtration, and ethanol was removed under reduced pressure. The residue was dissolved in 300 ml of ethyl acetate and washed successively with 1N hydrochloric acid, a saturated sodium hydrogencarbonate aqueous solution, and a saturated sodium chloride aqueous solution. The organic layer was dried over anhydrous sodium sulfate, and the solvent was removed under reduced pressure. The residue was purified by column chromatography on 200 g of silica gel using chloroform to 2% methanol/chloroform as an eluent to yield the titled compound 10 as a colorless crystal.

Melting point: 98°–103° C. $^1$H-NMR (CDCl$_3$) δ ppm: 1.62 (3H, d, J=7.2 Hz), 3.5 (1H, d, J=18 Hz), 3.9 (1H, d, J=18 Hz), 5.82 (1H, q, J=7.2 Hz), 7.36 (5H, s)

2) 5-[(1R)-Phenylethyl]-7-hydroxyimino-4-oxo-5-azaspiro[2.4]heptane 11:

To 3.35 g of 5-[(1R)-phenylethyl]-4,7-dioxo-5-azaspiro[2.4]heptane were added 1.6 g of hydroxylamine hydrochloride, 2.3 g of triethylamine, and 80 ml of ethanol, and the mixture was stirred at room temperature for 2 hours. The solvent was removed under reduced pressure. Chloroform was added to the residue, and the mixture was washed with a 10% citric acid aqueous solution and a saturated sodium chloride aqueous solution. The organic layer was dried over anhydrous sodium sulfate, and the solvent was removed under reduced pressure to give 3.5 g of the titled compound as a colorless crystal.

Melting point: 188°–194° C. $^1$H-NMR (CDCl$_3$) δ ppm: 1.2–1.4 (2H, m), 1.53 (3H, d, J=7.2 Hz & 2H, m), 3.8 (1H, d, J=18 Hz), 4.16 (1H, d, J=18 Hz), 5.63 (1H, q, J=7.2 Hz), 7.32 (5H, s)

3) 7-Amino-4-oxo-5-[(1R)-phenylethyl]-5-azaspiro[2.4]heptane 12a, 12b:

To 150 ml of methanol were added 3.5 g of 5-[(1R)-phenylethyl]-7-hydroxyimino-4-oxo-5-azaspiro[2.4]heptane and 7.5 ml of Raney nickel to conduct catalytic reduction. The catalyst was removed by filtration, and the solvent was removed under reduced pressure. The residue was subjected to column chromatography on 100 g of silica gel using 5% methanol/chloroform as an eluent to yield 1.0 g of the titled compound 12b (first eluted fraction) and 0.8 g of the titled compound 12a both as a colorless oily substance.

Compound 12b:
$^1$H-NMR (CDCl$_3$) δ ppm: 0.8–1.4 (4H, m), 1.52 (3H, d, J=7 Hz), 2.87 (1H, dd, J=10.3 Hz), 3.3–3.9 (2H, m), 4.27 (2H, br. s), 5.42 (1H, q, J=7 Hz), 7.29 (5H, s)

Compound 12a:
$^1$H-NMR (CDCl$_3$) δ ppm: 0.6–1.3 (4H, m), 1.40 (2H, s), 1.53 (3H, d, J=7.2 Hz), 2.99 (1H, dd, J=12.8, 7.2 Hz), 3.15–3.45 (2H, m), 5.52 (1H, q, J=7.2 Hz), 7.30 (5H, s)

4) 7-Amino-5-[(1R)-phenylethyl]-5-azaspiro[2.4]heptane 13a, 13b:

To 50 ml of anhydrous THF were added 1.0 g of compound 12b and 500 mg of lithium aluminum hydride, and the mixture was refluxed for 17 hours. After cooling, 0.5 ml of water, 0.5 ml of a 15% sodium hydroxide aqueous solution, and 1.5 ml of water were successively added to the reaction mixture, followed by stirring at room temperature for 30 minutes. An insoluble material was removed by filtration and thoroughly washed with THF. The filtrate and the washing were combined and dried. The solvent was removed under reduced pressure to yield 940 mg of the titled compound 13b as a pale yellow oily substance. In the similar manner, 755 mg of the titled compound 13a was obtained from 800 mg of compound 12a.

Compound 13b:
$^1$H-NMR (CDCl$_3$) δ ppm: 0.2–0.8 (4H, m), 1.35 (3H, d, J=6.6 Hz), 1.6–2.0 (2H, br. m), 2.2–3.1 (4H, m), 3.24 (1H, q, J=6.6 Hz), 3.5–3.9 (1H, m), 7.28 (5H, br. s)

Compound 13a:
$^1$H-NMR (CDCl$_3$) δ ppm: 0.3–0.9 (4H, m), 1.36 (3H, d, J=6.7 Hz), 1.8–2.2 (2H, m), 2.2–3.2 (4H, m), 3.24 (1H, q, J=6.7 Hz), 3.6–3.9 (1H, m), 7.28 (5H, br. s)

5) 7-(t-Butoxycarbonylamino)-5-[(1R)-phenylethyl]-5-azaspiro[2.4]heptane 14a, 14b:

To 20 ml of anhydrous THF were added 764 mg of compound 13b and 1.3 g of Boc-ON, and the mixture was stirred at room temperature for 4 hours. Ethyl acetate was added to the reaction mixture, and the mixture was washed twice with a 1N sodium hydroxide aqueous solution and then once with water, and extracted with a 10% citric acid aqueous solution. The aqueous layer was washed once with ethyl acetate, and a 15% sodium hydroxide aqueous solution was added thereto under cooling to made the solution alkaline. The solution was extracted three times with chloroform, and the organic layer was washed with a saturated sodium chloride aqueous solution and dried. The solvent was removed under reduced pressure, and the residue was purified by silica gel column chromatography (silica gel: 20 g; eluent: chloroform:methanol=20:1, 10:1) to yield 690 mg of the titled compound 14b. The product crystallized on being allowed to stand. The crystals were washed with n-hexane. The titled compound 14a was obtained in the similar manner.

Compound 14b:
Colorless crystal
Melting point: 103°–105° C. [α]$_D$: −15.2° (c=1.475, chloroform) $^1$H-NMR (CDCl$_3$) δ ppm: 0.4–0.9 (4H, m), 1.36 (3H, d, J=7.2 Hz), 1.44 (9H, s), 2.42 (2H, AB q, J=10.2 Hz), 2.79 (2H, d, J=5.6 Hz), 3.24 (1H, q, J=7.2 Hz), 3.6–4.0 (1H, m), 4.6–5.1 (1H, br. d), 7.28 (5H, s)

Elementary analysis for $C_{19}H_{28}N_2O_2$: Calcd.: C 72.12; H 8.92; N 8.85 Found: C 71.63; H 9.07; N 8.64

Compound 14a:
Colorless crystal
Melting point: 94°–97° C. [α]$_D$: +47.6° (c=0.89; chloroform) $^1$H-NMR (CDCl$_3$) δ ppm: 0.4–0.9 (4H, m), 1.33 (3H, d, J=6.6 Hz), 1.40 (9H, s), 2.29 (1H, d, J=9 Hz), 2.44 (1H, dd, J=10.8, 3.6 Hz), 2.77 (1H, d, J=9 Hz), 2.88 (1H, dd, J=10.8, 5.3 Hz), 3.22 (1H, q, J=6.6 Hz), 3.6–3.9 (1H, m), 4.7–5.2 (1H, br. d), 7.27 (5H, s)

Elementary analysis for $C_{19}H_{28}N_2O_2$: Calcd.: C 72.12; H 8.92; N 8.85 Found: C 71.86; H 9.36; N 8.68

6) 7-t-Butoxycarbonylamino-5-azaspiro[2.4]heptane 15a, 15b:

To 30 ml of ethanol were added 650 mg of compound 14b and 500 mg of 50% hydrous palladium-carbon, and catalytic reduction was conducted at 4.2 atm under heating. Six hours later, the catalyst was removed by filtration, and the solvent of the mother liquor was removed under reduced pressure. To the oily residue was added ethyl acetate, and the mixture was extracted twice with a 10% citric acid aqueous solution. The aqueous layer was made alkaline with a 15% sodium hydroxide aqueous solution and extracted three times with chloroform. The chloroform layer was washed with water and dried. The solvent was removed to yield 440 mg of the titled compound 15b as a crude product. In the similar manner, the titled compound 15a was obtained. The $^1$H-NMR spectra of both the compounds completely were identical with each other.

Compound 15b:
1H-NMR (CDCl$_3$) δ ppm: 0.4–1.0 (4H, m), 1.42 (9H, s), 2.71 (1H, d, J=10.2 Hz), 2.92 (1H, dd, J=10.8, 3.6 Hz), 3.01 (1H, d, J=10.2 Hz), 3.33 (1H, dd, J=10.8, 5.4 Hz), 3.5–3.9 (1H, m), 5.0–5.4 (1H, br. d)

Compound 15b was proved to be a 7-(S)-amino compound from X-ray analysis of the pyridonecarboxylic acid derivative derived therefrom.

EXAMPLE 1

Ethyl 3-[(1R,2S)-2-Fluorocyclopropylamino]-2-(2,3,4,5-tetrafluoro-6-methylbenzoyl)acrylate A mixture of 1.11 g of ethyl (2,3,4,5-tetrafluoro-6-methylbenzoyl)acetate, 1.19 g of ethyl orthoformate, and 5 ml of acetic anhydride was heated at 120° C. for 3.5 hours while stirring. After allowing to cool, the reaction mixture was concentrated and dried under reduced pressure.

In 3 ml of trifluoroacetic acid was dissolved 841 mg of (1R,2S)-1-(t-butoxycarbonylamino)-2-fluorocyclopropane at −5° C., and the solution was stirred at room temperature for 15 minutes. The reaction mixture was concentrated under reduced pressure and dried under reduced pressure overnight. The resulting oily substance was dissolved in 10 ml of dichloromethane and cooled to −5° C. Three milliliters of triethylamine was slowly added thereto dropwise. After completion of the dropwise addition, the mixture was further stirred at −5° C. for 5 minutes to give a pale yellow dichloromethane solution of (1R,2S)-2-fluorocyclopropylamine. To the resulting solution was added dropwise a solution of the above acrylic acid in 10 ml of dichloromethane while cooling with ice, followed by stirring at room temperature for 1 hour. The reaction mixture was washed with a 10% citric acid aqueous solution and water, dried over anhydrous sodium sulfate, and concentrated to give 1.26 g of the titled compound as a yellow amorphous compound.

EXAMPLE 2

Ethyl 1-[(1R,2S)-2-Fluorocyclopropyl]-6,7,8-trifluoro-5-methyl-4-oxo-1,4-dihydroquinoline-3-carboxylate In 10 ml of anhydrous dioxane was dissolved 1.15 g of ethyl 3-[(1R,2S)-2-fluorocyclopropylamino]-2-(2,3,4,5-tetrafluoro-6-methylbenzoyl)acrylate, and 190 mg of 60% sodium hydride in oil was added thereto, followed by stirring at room temperature for 30 minutes. The dioxane was concentrated to about half the volume, and the concentrate was added to 25 ml of 1N hydrochloric acid under cooling with ice. The crystals precipitated were collected by filtration, washed with diethyl ether, and dried to yield 1.05 g of the titled compound as a yellow crystal.

Melting point: 178°–180° C. (decomposition)

EXAMPLE 3

1-[(1R,2S)-2-Fluorocyclopropyl]-6,7,8-trifluoro-5-methyl-4-oxo-1,4-dihydroquinoline-3-carboxylic Acid A mixture of 1.00 g of ethyl 1-[-(1R,2S)-2-fluorocyclopropyl]-6,7,8-trifluoro-5-methyl-4-oxo-1,4-dihydroquinoline-3-carboxylate, 10 ml of concentrated hydrochloric acid, and 20 ml of acetic acid was heated under reflux for 1 hour and, after allowing to cool, water was added thereto. The precipitated crystals were collected by filtration, washed with water and ethanol, and dried to yield 960 mg of the titled compound as a pale yellow powderous crystal, which was then recrystallized from a mixed solvent of ethanol and chloroform.

Melting point: 237°–240° C. (decomposition)

EXAMPLE 4

Ethyl 3-[(1R,2S)-2-Fluorocyclopropylamino]-2-(2,4,5-trifluoro-6-methylbenzoyl)acrylate A mixture of 1.88 g of ethyl (2,4,5-trifluoro-6-methylbenzoyl)acetate, 2.4 ml of ethyl orthoformate, and 8 ml of acetic anhydride was heated at 120° C. for 1.5 hours with stirring. After allowing to cool, the reaction mixture was concentrated and dried under reduced pressure to yield a yellow oily substance.

In 5 ml of trifluoroacetic acid was dissolved 1.50 g of (1R,2S)-2-(t-butoxycarbonylamino)-2-fluorocyclopropane at −5° C., and the solution was stirred at room temperature for 15 minutes. The reaction mixture was concentrated under reduced pressure and dried in vacuo overnight. The resulting oily substance was dissolved in 20 ml of dichloromethane and, after cooling to −5° C., 5 ml of triethylamine was slowly added dropwise thereto. After the addition, the reaction mixture was further stirred at −5° C. for 5 minutes to yield a pale yellow solution of (1R,2S)-2-fluorocyclopropylamine in dichloromethane. To the resulting solution was added dropwise a solution of the above acrylic acid in 20 ml of dichloromethane while cooling with ice, followed by stirring at room temperature for 1 hour. The reaction mixture was washed with a 10% citric acid aqueous solution and water, dried over anhydrous sodium sulfate, and concentrated to yield 2.47 g of the titled compound as a yellowish orange oily substance.

EXAMPLE 5

Ethyl 6,7-Difluoro-1-[(1R,2S)-2-fluorocyclopropyl]-5-methyl-4-oxo-1,4-dihydroquinoline-3-carboxylate In 25 ml of anhydrous dioxane was dissolved 2.40 g of ethyl 3-[(1R,2S)-2-fluorocyclopropylamino]-2-(2,4,5-trifluoro-6-methylbenzoyl)acrylate, and 338 mg of 60% sodium hydride in oil was added thereto under cooling with ice, followed by stirring at room temperature for 1 hour. The reaction mixture was poured into a mixture of 50 ml of 1N hydrochloric acid and 50 ml of dichloromethane, followed by stirring. The organic layer was separated. The aqueous layer was extracted with 100 ml of dichloromethane, and the extract was combined with the organic layer. The combined organic layer was dried over anhydrous sodium sulfate, the dichloromethane was removed by distillation, and the residue was dried in vacuo to yield yellow crude crystals. The crude crystals to yield with diethyl ether, filtered, and dried to yield 1.76 g of the titled compound as a pale yellow powder. The product was recrystallized from acetonitrile.

Melting point: 243°–244° C. (decomposition)

EXAMPLE 6

6,7-Difluoro-1-[(1R,2S)-2-fluorocyclopropyl]-5-methyl-4-oxo-1,4-dihydroquinoline-3-carboxylic Acid A mixture of 1.70 g of ethyl 6,7-difluoro-1-[(1R,2S)-2-fluorocyclopropyl]-5-methyl-4-oxo-1,4-dihydroquinoline-3-carboxylate, 30 ml of concentrated hydrochloric acid, and 60 ml of acetic acid was heated under reflux for 1.5 hours. After allowing to cool, water was added to the reaction mixture. The precipitated crystals were collected by filtration, washed with water and ethanol, and dried. Recrystallization from a mixed solvent of ethanol and chloroform yielded 990 mg of the titled compound as a pale yellow powder.

Melting point: 249°–250° C. (decomposition)

EXAMPLE 7

7-[3-(S)-Aminopyrrolidinyl]-6,8-difluoro-1-[(1R,2S)-2-fluorocyclopropyl]-5-methyl-4-oxo-1,4-dihydroquinoline-3-carboxylic Acid A mixture of 100 mg of 6,7,8-trifluoro-1-[(1R,2S)-2-fluorocyclopropyl]-5-methyl-4-oxo-1,4-dihydroquinoline- 3-carboxylic acid, 120 mg of (S)-3-t-butoxycarbonylaminopyrrolidine, and 3 ml of anhydrous dimethyl sulfoxide was heated at 100° to 120° C. for 1 hour with stirring, and dimethyl sulfoxide was removed under reduced pressure. Water was added to the residue, and the precipitated yellow crystals were collected by filtration. Three milliliters of trifluoroacetic acid was stirred under ice-cooling, and the above-obtained yellow crystals were slowly added thereto, followed by stirring at room temperature for 30 minutes. The trifluoroacetic acid was removed under reduced pressure, and the residue was dissolved in a 1N sodium hydroxide aqueous solution (pH 12). The solution was neutralized with 1N hydrochloric acid and extracted with chloroform. The extract was dried over anhydrous sodium sulfate. The chloroform was removed under reduced pressure, and the residue was recrystallized from a mixed solvent of ethanol and aqueous ammonia. The resulting crystals were collected by filtration, washed with ethanol, and dried to yield 83 mg of the titled compound as a pale yellow crystal.

Melting point: 120°–123° C. (decomposition) Elementary analysis for $C_{18}H_{18}F_3N_3O_3 \cdot \frac{1}{2}H_2O$: Calcd.: C 55.38; H 4.91; N 10.76 Found: C 55.44; H 4.83; N 10.54 $[\alpha]_D$: +17.99° (c=0.675, 1N NaOH)

EXAMPLE 8

7-[3-(R)-Aminopyrrolidinyl]-6,8-difluoro-1-[(1R,2S)-2-fluorocyclopropyl]-5-methyl-4-oxo-1,4-dihydroquinoline-3-carboxylic Acid A hundred milligrams of 6,7,8-trifluoro-1-[(1R,2S)-2-fluorocyclopropyl]-5-methyl-4-oxo-1,4-dihydroquinoline-3-carboxylic acid and 120 mg of (R)-3-t-butoxycarbonylaminopyrrolidine were reacted in the same manner as in Example 7, and the reaction mixture was worked up similarly to yield 80 mg of the titled compound as a grayish white to yellowish white substance.

Melting point: 151°–153° C. (decomposition) Elementary analysis for $C_{18}H_{18}F_3N_3O_3 \cdot \frac{1}{4}H_2O$: Calcd.: C 54.75; H 5.19; N 10.64 Found: C 54.93; H 5.40; N 10.64 $[\alpha]_D$: -262.35° (c=0.875, 1N NaOH)

EXAMPLE 9

7-[7-(S)-Amino-5-azaspiro[2.4]heptan-5-yl]-6,8-difluoro-1-[(1R,2S)-2-fluorocyclopropyl]-5-methyl-4-oxo-1,4-dihydroquinoline-3-carboxylic Acid A mixture of 400 mg of 6,7,8-trifluoro-1-[(1R,2S)-2-fluorocyclopropyl]-5-methyl-4-oxo-1,4-dihydroquinoline-3-carboxylic acid, 405 mg of 7-(S)-t-butoxycarbonylamino-5-azaspiro[2.4]heptane, and 10 ml of anhydrous dimethyl sulfoxide was heated at 120° C. for 1 hour with stirring. After allowing to cool, the reaction mixture was concentrated under reduced pressure, and water was added to the residue. The precipitated yellow crystals were collected by filtration and dried. Five milliliters of trifluoroacetic acid was stirred under cooling with ice, and the above-obtained yellow crystals were added thereto, followed by stirring at room temperature for 1 hour. The reaction mixture was worked up in the same manner as in Example 7. The resulting crude crystals were recrystallized from a mixed solvent of ethanol and 28% aqueous ammonia to yield 263 mg of the titled compound as a pale yellow powder.

Melting point: 151°–153° C. (decomposition) Elementary analysis for $C_{20}H_{20}F_3N_3O_3 \cdot \frac{1}{4}H_2O$: Calcd.: C 58.32; H 5.02; N 10.20 Found: C 58.54; H 5.04; N 10.04 $[\alpha]_D$: -20.80° (c=1.040; 1N NaOH)

EXAMPLE 10

7-[7-(S)-Amino-5-azaspiro[2.4]heptan-5-yl]-6-fluoro-1-[(1R,2S)-2-fluorocyclopropyl]-5-methyl-4-oxo-1,4-dihydroquinoline-3-carboxylic Acid A mixture of 200 mg of 6,7-difluoro-1-[(1R,2S)-2-fluorocyclopropyl]-5-methyl-4-oxo-1,4-dihydroquinoline-3-carboxylic acid, 287 mg of 7-(S)-t-butoxycarbonylamino-5-azaspiro[2.4]heptane, and 5 ml of anhydrous dimethyl sulfoxide was heated at 100° C. for 30 minutes with stirring. After allowing to cool, the reaction mixture was concentrated under reduced pressure, and water was added to the residue. The precipitated yellow crystals were collected by filtration and added to 5 ml of trifluoroacetic acid while stirring and cooling with ice, followed by stirring at room temperature for 30 minutes. The reaction mixture was further worked up in the same manner as in Example 7. Recrystallization of the crude crystal from ethanol gave 122 mg of the titled compound as a pale yellow powder.

Melting point: 143°–145° C. (decomposition) Elementary analysis for $C_{20}H_{21}F_2N_3O_3 \cdot \frac{1}{4}H_2O$: Calcd.: C 60.98; H 5.50; N 10.67 Found : C 61.22; H 5.50; N 10.54 $[\alpha]_D$: -18.18° (c=0.427, 1N NaOH)

EXAMPLE 11

7-(1,4-Diazabicyclo[3.2.1]octan-4-yl)-6-fluoro-1-[2-(S)-fluoro-1-(R)-cyclopropyl]-5-methyl-4-oxo-1,4-dihydroquinoline-3-carboxylic Acid To 6 ml of dried N,N-dimethylformamide were added 200 mg of 6,7-difluoro-1-[2-(S)-fluoro-1-(R)-cyclopropyl]-5-methyl-4-oxo-1,4-dihydroquinoline-3-carboxylic acid, 372 mg of 1,4-diazabicyclo[3.2.1]octane dihydrochloride, and 2 ml of triethylamine, and the mixture was stirred at 100° C. for 1 hour. After allowing to cool, the reaction mixture was concentrated under reduced pressure, and the residue was dissolved in a 1N sodium hydroxide aqueous solution under cooling with ice. The solution was neutralized with 1N hydrochloric acid and extracted with chloroform. The extract was dried over anhydrous sodium sulfate, and the solvent was removed under reduced pressure. The resulting crude crystals were recrystallized from a mixed solvent of ethanol and 28% aqueous ammonia, and the crystals were collected by filtration, washed with diethyl ether, and dried at 60° C. under reduced pressure overnight to yield 131 mg of the titled compound as a yellow powder.

Melting point: 233°–235° C. (decomposition) Elementary analysis for $C_{20}H_{21}F_2N_3O_3 \cdot \frac{1}{4}H_2O$: Calcd.: C 60.98; H 5.50; N 10.66 Found: C 61.11; H 5.44; N 10.46

EXAMPLE 12

7-(1,4-Diazabicyclo[3.2.1]octan-4-yl)-6,8-difluoro-1-[2-(S)-fluoro-1-(R)-cyclopropyl]-5-methyl-4-oxo-1,4-dihydroquinoline-3-carboxylic Acid To 5 ml of dried N,N-dimethylformamide were added 211 mg of 6,7,8-trifluoro-1-[2-(S)-fluoro-1-(R)-cyclopropyl]-5-methyl-4-oxo-1,4-dihydroquinoline-3-carboxylic acid, 372 mg of 1,4-diazabicyclo[3.2.1]octane dihydrochloride, and 2 ml of triethylamine, and the mixture was stirred at 100° C. for 1 hour. After allowing to cool, the reaction mixture was concentrated under reduced pressure, and the residue was dissolved in a 1N sodium hydroxide aqueous solution while cooling with ice. After neutralizing with 1N hydrochloric acid, the mixture was extracted with chloroform, and the extract was dried over anhydrous sodium sulfate. The solvent was removed under reduced pressure, and the resulting crude crystals were recrystallized from a mixed solvent of ethanol and 28% aqueous ammonia. The precipitated crystals were collected by filtration, washed with diethyl ether, and dried at 60° C. in vacuo overnight to yield 170 mg of the titled compound as a yellow powder.

Melting point: 257°–259.5° C. (decomposition) Elementary analysis for $C_{20}H_{20}F_3N_3O_3 \cdot \frac{1}{2}H_2O$: Calcd.: C 57.69; H 5.08; N 10.09 Found: C 57.64; H 5.15; N 9.89

TABLE 1

| Test Microorganism | Test Compound | | | |
|---|---|---|---|---|
| | Example 7 | Example 8 | Example 9 | Example 10 |
| E. coli NIHJ | 0.006 | 0.006 | 0.006 | 0.013 |
| Sh. flexneri 2a5503 | 0.006 | 0.013 | 0.006 | 0.013 |
| Pr. vulgaris 08601 | 0.013 | 0.025 | 0.025 | 0.025 |
| Pr. mirabilis IFO3849 | 0.05 | 0.1 | 0.1 | 0.05 |
| Ser. marcescens 10100 | 0.05 | 0.05 | 0.05 | 0.006 |
| Ps. aeruginosa 32104 | 0.05 | 0.1 | 0.05 | 0.05 |
| Ps. aeruginosa 32121 | 0.025 | 0.1 | 0.05 | 0.025 |
| Ps. cepacia IID1340 | 0.2 | 0.39 | 0.2 | 0.2 |
| Ps. maltophilia IID1275 | 0.05 | 0.1 | 0.025 | 0.05 |
| Staph. aureaus 209P | 0.025 | 0.05 | 0.013 | 0.025 |
| Staph. epidermidis 56500 | 0.05 | 0.05 | 0.05 | 0.025 |
| Stc. pyogenes G-36 | 0.2 | 0.39 | 0.1 | 0.1 |
| Stc. faecalis | 0.1 | 0.2 | 0.1 | 0.1 |

The structures of the compounds of Examples 7 to 10 are shown below.

EXAMPLE 7

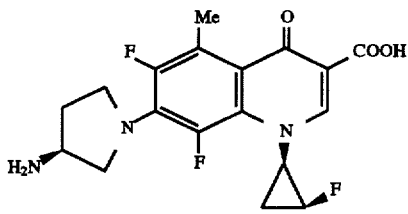

EXAMPLE 8

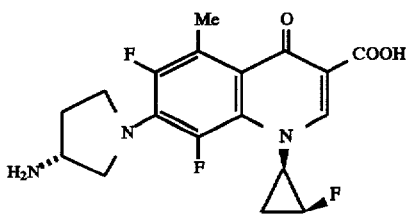

EXAMPLE 9

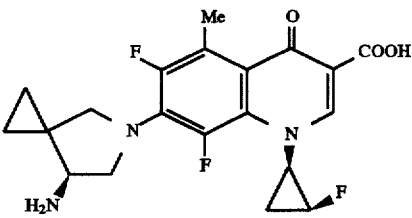

EXAMPLE 10

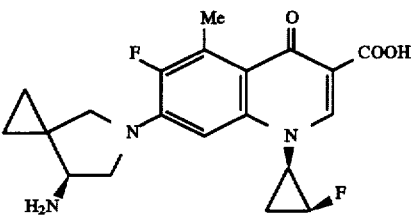

INDUSTRIAL UTILITY

The compounds of the present invention exhibit potent antimicrobial activity and are therefore useful as drugs for humans, animals and fishes, agricultural chemicals, and food preservatives.

What is claimed is:

1. A compound represented by formula (I) or a salt thereof:

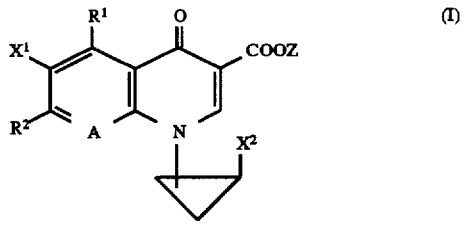

wherein $R^1$ represents a methyl group, an ethyl group, a propyl group, an isopropyl group, a fluoromethyl group or a difluoromethyl group;

$R^2$ represents a substituent represented by the following formula:

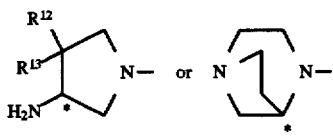

wherein $R^{12}$ and $R^{13}$ together form a polymethylene chain to provide a 3- or 6-membered ring;

A represents $C-X^3$;

$X^1$ and $X^2$ each represents a halogen atom;

$X^3$ represents a hydrogen atom, a halogen atom, a cyano group, a trifluoromethyl group, an alkyl group having from 1 to 6 carbon atoms or an alkyloxy group having from 1 to 6 carbon atoms; and Z represents a hydrogen atom.

2. A compound and a salt thereof as claimed in claim 1, wherein $R^2$ in the formula is a saturated nitrogen-containing heterocyclic ring consisting of a single stereoisomer.

3. A compound and a salt thereof as claimed in claim 1, or 2, wherein the 1,2-cis-2-halogenocyclopropyl group in the formula is a substituent composed of a single stereochemical form.

4. A compound and a salt thereof as claimed in claim 3, wherein said 1,2-cis-2-halogenocyclopropyl group is a (1R, 2S)-2-halogenocyclopropyl group.

5. A compound and a salt thereof as claimed in claim 4, wherein $R^2$ in the formula is a 7-amino-5-azaspiro[2.4]heptan-5-yl group.

6. A compound and a salt thereof as claimed in claim 1, 2, 3, 4 or 5, wherein $X^2$ is a fluorine atom.

7. A compound selected from the group consisting of 7-[7-amino-5-azaspiro[2.4]heptan-5-yl]-6,8-difluoro-1-(1,2-cis-2-fluorocyclopropyl)-5-methyl-4-oxo-1,4-dihydroquinoline-3-carboxylic acid, and 7-(7-amino-5-azaspiro[2.4]heptan-5-yl)-6-fluoro-1-(1,2-cis-2-fluorocyclopropyl)-5-methyl-4-oxo-1,4-dihydroquinoline-3-carboxylic acid, or a salt thereof.

8. A compound or a salt thereof as claimed in claim 7, wherein the selected compound is a compound consisting of a single diastereomer.

9. 7-[7-(S)-Amino-5-azaspiro[2.4]heptan-5-yl]-6,8-difluoro-1-[(1R,2S)-2-fluorocyclopropyl]-5-methyl-4-oxo-1,4-dihydroquinoline-3-carboxylic acid.

10. 7-[7-(S)-Amino-5-azaspiro[2.4]heptan-5-yl]-6-fluoro-1-[(1R,2S)-2-fluorocyclopropyl]-5-methyl-4-oxo-1,4-dihydroquinoline-3-carboxylic acid.

11. An antimicrobial composition comprising an antimicrobial effective amount of the compound claimed in claim 1 and a pharmaceutically acceptable carrier.

* * * * *